(12) United States Patent
Guerrero et al.

(10) Patent No.: US 9,408,896 B2
(45) Date of Patent: Aug. 9, 2016

(54) VACCINATION OF COMPANION ANIMALS TO ELICIT A PROTECTIVE IMMUNE RESPONSE AGAINST TICK INFESTATIONS AND TICK-BORNE PATHOGEN TRANSMISSION

(71) Applicant: The United States of America, as Represented by the Secretary of Agriculture, Washington, DC (US)

(72) Inventors: Felicito Guerrero, Boerne, TX (US); Adalberto A. Perez De Leon, Kerrville, TX (US); Lane D. Foil, Baton Rouge, LA (US)

(73) Assignees: The United States of America, as represented by the Secretary of Agriculture, Washington, DC (US); Louisiana State University Agricultural Center, Baton Rouge, LA (US)

( * ) Notice: Subject to any disclaimer, the term of this patent is extended or adjusted under 35 U.S.C. 154(b) by 2 days.

(21) Appl. No.: 14/200,502

(22) Filed: Mar. 7, 2014

(65) Prior Publication Data

US 2014/0271702 A1   Sep. 18, 2014

Related U.S. Application Data

(60) Provisional application No. 61/779,040, filed on Mar. 13, 2013.

(51) Int. Cl.
*A61K 39/00* (2006.01)

(52) U.S. Cl.
CPC ....... *A61K 39/0003* (2013.01); *A61K 2039/552* (2013.01); *A61K 2039/55566* (2013.01)

(58) Field of Classification Search
None
See application file for complete search history.

(56) References Cited

U.S. PATENT DOCUMENTS

| 8,722,063 B2 | 5/2014 | Guerrero, Jr. et al. |
| 2004/0052807 A1 | 3/2004 | Salcedo et al. |
| 2007/0031411 A1 | 2/2007 | Trimnell et al. |
| 2010/0278752 A1 | 11/2010 | Kotsyfakis et al. |

OTHER PUBLICATIONS

Cruse et al., Illustrated Dict. of Immunology, 2nd ed., CRC Press, 2003, p. 46.*
McGuinness et al. (Mol. Microbiol., 7:505-514, 1993.*
Moudallal et al. (EMBO Journal, 1:1005-1010, 1982).*
Abaza et al. (J. Prot. Chem., 11:433-444, 1992).*
Ball, Andrew et al., "Identification, functional characterization and expression patterns of a water-specific aquaporin in the brown dog tick, Rhipicephalus sanguineus", Insect Biochemistry and Molecular Biology, (2009) 39:105-112.
Seixas, Adriana et al., "Rhipicephalus (Boophilus) microplus embryo proteins as target for tick vaccine" (2012) 148:149-156.
Campbell, Ewan M., et al., "Role of an aquaporin in the sheep tick Ixodes ricinus: Assessment as a potential control target", International Journal for Parasitology, 40, 2010, pp. 15-23.
Guerrero, F.D., et al., "BmiGI: A database of cDNAs expressed in Boophilus microplus, the tropical/southern cattle tick", Insect Biochemistry and Molecular Biology, 35, 2005, pp. 585-595.
Guerrero, Felix D., et al., "Sequencing a New Target Genome: The Boophilus microplus (Acari: Ixodidae) Genome Project", Journal of Medical Entomology, vol. 43, No. 1, Jan. 2006, pp. 9-16.
Guerrero, Felix D., et al., "Use of an Allelle-Specific Polymerase Chain Reaction Assay to Genotype Pyrethroid Resistant Strains of Boophilus microplus (Acari: Ixodidae)", Journal of Medical Entomology, vol. 38, No. 1, Jan. 2001, pp. 44-50.
Nuttall, P.A., et al., "Exposed and concealed antigens as vaccine targets for controlling ticks and tick-borne diseases", Parasite Immunology, 2006, 28, pp. 155-163.
Rachinsky, Anna, et al., "Proteomic profiling of Rhipicephalus (Boophilus) microplus midgut responses to infection with Babesia bovis", Veterinary Parasitology, 152, 2008, pp. 294-313.
Sunter, Jack D., et al., "A novel SINE family occurs frequently in both genomic DNA and transcribed sequences in ixodid ticks of the arthropod sub-phylum Chelicerata", Gene, 415, 2008, pp. 13-22.

* cited by examiner

*Primary Examiner* — Brian J Gangle
(74) *Attorney, Agent, or Firm* — John D. Fado; David L. Marks

(57) ABSTRACT

Compositions of either the aquaporin protein from the cattle tick, *Rhipicephalus microplus*, or a nucleic acid construct incorporating a nucleic acid sequence encoding this aquaporin protein, are effective for eliciting a protective immune response against other tick species in non-bovine animals. The *R. microplus* aquaporin protein is antigenic and can be administered as a protein vaccine, or in the alternative, the nucleic acid construct can be utilized as a DNA vaccine. Induction of the immune response significantly reduces or eliminates the infestation of treated, non-bovine animals with ticks other than the cattle tick, particularly the brown dog tick, *Rhipicephalus sanguineus*. Moreover, as ticks are vectors of a variety of pathogenic agents, the reduction in the incidence of tick infestation afforded by the vaccines may concurrently reduce the incidence of diseases caused by these pathogenic agents in susceptible animals.

10 Claims, 5 Drawing Sheets

Figure 1A
MKIENLLIRQLINEFLGTMILITIGDSIMAIIIAGDNESLAACVGPLGWGVAIYVAVQISGGVS
SHLNPAVTLAQASVRKFPIAKVPLYFAAQYLGGFVGAALVFATYKDAIEHFDQGIRQVTGE
KATAGIFATYPRPHVSTLTCFIDQVIATGIMMVCVEAIGDTRNFGGIPPHIHPICLGLMIMAI
IFSFAYNCMCPL Figure 1B
MRFPSIFTAVLFAASSALAAPVNTTTEDETAQIPAEAVIGYSDLEGDFDVAVLPFSNSTNN
GLLFINTTIASIAAKEEGVSLEKREAEAEFMKIENLLIRQLINEFLGTMILITIGDSIMAIIIAG
DNESLAACVGPLGWGVAIYVAVQISGGVSSHLNPAVTLAQASVRKFPIAKVPLYFAAQYLG
GFVGAALVFATYKDAIEHFDQGIRQVTGEKATAGIFATYPRPHVSTLTCFIDQVIATGIMM
VCVEAIGDTRNFGGIPPHIHPICLGLMIMAIIFSFAYNCMCPAAASFLEQKLISEEDLNSAVD
HHHHHH*

Figure 1C
MEIENLLIRQLINEFLGTMILITIGDSIMAIIIAGDNESLAACVGPLGWGVAIYVAVQISGGVS
SHLNPAVTLAQASVRKFPIAKVPLYFAAQYLGGFVGAALVFATYKDAIEHFDQGIRQVTGE
KATAGIFATYPRPHVSTLTCFIDQVIATGIMMVCVEAIGDTRNFGGIPPHIHPICLGLMIMAI
IFSFAYNCMCLESRGPFEQKLISEEDLNMHTGHHHHHH*

Figure 2A
AAGCAGTGGTATCAACGCAGAGTACGCGGGGGGGCTGGGAAAAGCTGCTAGCATCAACT
CGGCTTCTAGCTTGGGGTCTCGCACCGCGCCTCGAGCCCGACCAGCCTGCGGTGGCGCCGT
CTCGCTGAAAGGGGGAAAGAGGAAAGAGAAAGAAGAAAAGAAAAATATCGCCGGCATCG
GCGACGAAGGCGGAGCAGCAATGCGATCGTCAGAGCACGCATTTCGACGGTGAGATTCGG
AAGCTCGAAGGCGTCGCCGGCACTGCGAGAAAGCCGGTGAAGTACTTTGGGACCGCCGCG
TAGGCGTCTTGACAGTCCGCTCCCGAGGCAACGACGACACGCTCCAAGATGAAGATCGAG
AACCTGCTCATACGGCAGCTCATCAACGAGTTCCTCGGAACAATGATTCTAATTACTATC
GGCGACTCCATCATGGCCATCATCATCGCCGGTGACAACGAGTCTCTGGCTGCTTGCGTG
GGGCCCTTGGGATGGGCGTCGCCATCTACGTGGCCGTGCAAATCTCCGGAGGAGTCTCG
TCCCACCTGAATCCTGCCGTGACGCTGGCCCAGGCGTCCGTGCGCAAGTTTCCGATCGCCA
AAGTGCCGCTATACTTCGCGGCTCAGTACCTGGGTGGCTTCGTCGGTGCGGCGCTCGTGT
TTGCCACCTACAAAGACGCTATTGAACACTTCGACCAGGGAATCCGCCAAGTGACGGGAG
AGAAGGCCACGGCTGGTATATTTGCAACTTACCCCAGACCACACGTCTCCACTCTGACCT
GCTTCATTGATCAGGTCATCGCAACGGGCATAATGATGGTGTGCGTCGAGGCCATCGGCG
ACACTCGCAACTTCGGCGGCATTCCGCCGCACATTCACCCAATCTGCTTGGGTCTCATGA
TCATGGCTATTATCTTCAGTTTCGCCTACAACTGCATGTGCCCGCTC Figure 2B
ATGAGATTTCCTTCAATTTTTACTGCTGTTTTATTCGCAGCATCCTCCGCATTAGCTGCT
CCAGTCAACACTACAACAGAAGATGAAACGGCACAAATTCCGGCTGAAGCTGTCATCGGT
TACTCAGATTTAGAAGGGGATTTCGATGTTGCTGTTTTGCCATTTTCCAACAGCACAAAT
AACGGGTTATTGTTTATAAATACTACTATTGCCAGCATTGCTGCTAAAGAAGAAGGGGT
ATCTCTCGAGAAAGAGAGGCTGAAGCTGAATTCATGAAGATCGAGAACCTGCTCATAC
GGCAGCTCATCAACGAGTTCCTCGGAACAATGATTCTAATTACTATCGGCGACTCCATCA
TGGCCATCATCATCGCCGGTGACAACGAGTCTCTGGCTGCTTGCGTGGGGCCCTTGGGAT
GGGGCGTCGCCATCTACGTGGCCGTGCAAATCTCCGGAGGAGTCTCGTCCCACCTGAATC
CTGCCGTGACGCTGGCCCAGGCGTCCGTGCGCAAGTTTCCGATCGCCAAAGTGCCGCTAT
ACTTCGCGGCTCAGTACCTGGGTGGCTTCGTCGGTGCGGCGCTCGTGTTTGCCACCTACA
AAGACGCTATTGAACACTTCGACCAGGGAATCCGCCAAGTGACGGGAGAGAAGGCCACG
GCTGGTATATTTGCAACTTACCCCAGACCACACGTCTCCACTCTGACCTGCTTCATTGAT
CAGGTCATCGCAACGGGCATAATGATGGTGTGCGTCGAGGCCATCGGCGACACTCGCAAC
TTCGGCGGCATTCCGCCGCACATTCACCCAATCTGCTTGGGTCTCATGATCATGGCTATT
ATCTTCAGTTTCGCCTACAACTGCATGTGCCCGGCGGCCGCAGCTTTCTAGAACAAAAA
CTCATCTCAGAAGAGGATCTGAATAGCGCCGTCGACCATCATCATCATCATTGA

Figure 2C

AAGATGGAGATCGAGAACCTGCTCATACGGCAGCTCATCAACGAGTTCCTCGGAACAATG
ATTCTAATTACTATCGGCGACTCCATCATGGCCATCATCATCGCCGGTGACAACGAGTCT
CTGGCTGCTTGCGTGGGGCCCTTGGGATGGGGCGTCGCCATCTACGTGGCCGTGCAAATC
TCCGGAGGAGTCTCGTCCCACCTGAATCCTGCCGTGACGCTGGCCCAGGCGTCCGTGCGC
AAGTTTCCGATCGCCAAAGTGCCGCTATACTTCGCGGCTCAGTACCTGGGTGGCTTCGTC
GGTGCGGCGCTCGTGTTTGCCACCTACAAAGACGCTATTGAACACTTCGACCAGGGAATC
CGCCAAGTGACGGGAGAGAAGGCCACGGCTGGTATATTTGCAACTTACCCCAGACCACAC
GTCTCCACTCTGACCTGCTTCATTGATCAGGTCATCGCAACGGGCATAATGATGGTGTGC
GTCGAGGCCATCGGCGACACTCGCAACTTCGGCGGCATTCCGCCGCACATTCACCCAATC
TGCTTGGGTCTCATGATCATGGCTATTATCTTCAGTTTCGCCTACAACTGCATGTGCCTC
GAGTCTAGAGGGCCCTTCGAACAAAAACTCATCTCAGAAGAGGATCTGAATATGCATAC
CGGTCATCATCACCATCACCATTGA

Figure 3

ATGAAGATTGAGAACTTGTTGATTAGACAATTGATTAACGAGTTCTTGGGTACTATGAT
TTTGATTACTATTGGTGACTCTATTATGGCTATTATTATTGCTGGTGACAACGAGTCTTT
GGCTGCTTGCGTTGGTCCATTGGGTTGGGGTGTTGCTATTTACGTTGCTGTTCAAATTTC
TGGTGGTGTTTCTTCTCACTTGAATCCAGCTGTTACTTTGGCTCAAGCTTCTGTTAGAAA
GTTTCCAATTGCTAAAGTTCCATTGTACTTCGCTGCTCAATACTTGGGTGGTTTCGTTGG
TGCTGCTTTGGTTTTTGCTACTTACAAAGACGCTATTGAACACTTCGACCAAGGTATTAG
ACAAGTTACTGGTGAGAAGGCTACTGCTGGTATTTTTGCTACTTACCCAAGACCACACGT
TTCTACTTTGACTTGCTTCATTGATCAAGTTATTGCTACTGGTATTATGATGGTTTGCGT
TGAGGCTATTGGTGACACTAGAAACTTCGGTGGTATTCCACCACACATTCACCCAATTTG
CTTGGGTTTGATGATTATGGCTATTATTTTCTCTTTCGCTTACAACTGCATGTGCC

VACCINATION OF COMPANION ANIMALS TO ELICIT A PROTECTIVE IMMUNE RESPONSE AGAINST TICK INFESTATIONS AND TICK-BORNE PATHOGEN TRANSMISSION

CROSS REFERENCE TO RELATED APPLICATION

This application claims priority to U.S. Patent Application 61/779,040 filed Mar. 13, 2013.

BACKGROUND OF THE INVENTION

1. Field of the Invention

The invention relates methods to control and prevent tick infestations in treated non-bovine animals, including domestic dogs, which further protects the animals against the transmission of tick-borne pathogens. Vaccine compositions are prepared from the aquaporin protein from the cattle tick, *Rhipicephalus microplus*, or from a nucleic acid construct comprising a nucleic acid sequence encoding this aquaporin protein.

2. Description of the Prior Art

Ticks pose a significant risk to the health and welfare of warm-blooded animals as the vectors for a large number of pathogenic agents, including protozoan parasites, viruses and bacteria. For instance, the brown dog tick, *Rhipicephalus sanguineus*, is the primary reservoir and vector of canine ehrlichiosis, a lethal disease caused by the blood-borne intracellular bacterial pathogen, *Ehrlichia canis*, and canine babesiosis, caused by the intraerythrocytic protozoan parasites *Babesia canis* and *Babesia gibsoni*. Canine ehrlichiosis occurs throughout the world and is endemic in the United States, infecting dogs of all breeds and ages. Cats and humans may be infected with *E. canis* as well. The brown dog tick can also transmit Rocky Mountain spotted fever to humans. Ticks are also carriers of a number of other common tick-borne infectious disease agents such as tick-borne encephalitis virus, Crimean-Congo hemorrhagic fever virus, Nairobi sheep virus, *Borrelia burgdorferi* (the agent of Lyme disease), *Theileria parva* (the agent of East Coast fever), and parasites of the genus *Babesia* (including the agents of babesiosis or cattle fever in bovine), as well as other injurious effects that have major impacts in human and veterinary medicine.

Presently, efforts to control these pests have primarily relied upon the use of pesticides. However, an increase in the resistance of ticks to approved acaricides and insecticides threatens efforts to control these pests in the U.S. and elsewhere.

As a result of the spread of pesticide-resistant strains of these and other ticks and flies, there is a growing need to develop improved tools for their control. Attempts have been made to use immunological means of control through vaccine technology. Some success has been met in identifying certain protective antigens of arthropod parasites as being potential vaccine candidates, but only a few have as yet come to commercial fruition, most notably the BM86 vaccine for the cattle tick *Rhipicephalus (Boophilus) microplus*. Despite these developments, there is nonetheless a continuing need for arthropod parasite vaccines and in particular for a vaccine which may be used against ticks, including the brown dog tick.

SUMMARY OF THE INVENTION

We have discovered that compositions of either the aquaporin protein from the cattle tick, *Rhipicephalus microplus*, or a nucleic acid construct incorporating a nucleic acid sequence encoding this aquaporin protein, are effective for eliciting a protective immune response against other tick species in non-bovine animals. The *R. microplus* aquaporin protein is antigenic and can be administered as a protein vaccine, or in the alternative, the nucleic acid construct can be utilized as a DNA vaccine. In this later embodiment, the nucleic acid constructs are administered to a subject animal such that the aquaporin protein is expressed in vivo within the cells of the vaccinated animal. Induction of the immune response significantly reduces or eliminates the infestation of treated, non-bovine animals with ticks other than the cattle tick, particularly the brown dog tick, *Rhipicephalus sanguineus*. Moreover, as ticks are vectors of a variety of pathogenic agents, the reduction in the incidence of tick infestation afforded by the vaccines may concurrently reduce the incidence of diseases caused by these pathogenic agents in susceptible animals.

In accordance with this discovery, it is an object of this invention to provide protective vaccines against ticks other than the cattle tick, *R. microplus*, in non-bovine animals.

Another object of the invention is to provide protective vaccines that control and prevent infestations with ticks of different species than the cattle tick, and in animals different from bovine.

A further object of the invention is to provide protective vaccines against the brown dog tick, *R. sanguineus*, in animals.

Yet another object of the invention is to provide protective vaccines against the brown dog tick, *R. sanguineus*, in companion animals, including deer, horses, domestic dogs and cats.

Still another object of the invention is to provide protective vaccines that control and prevent animal infestations with ticks, and thereby reduce or eliminate the incidence of diseases caused by pathogenic agents carried by the ticks.

Still another object of the invention is to provide protective vaccines that control and prevent canine infestations with the brown dog tick, *R. sanguineus*, and thereby reduce or eliminate the incidence of canine ehrlichiosis caused by *Ehrlichia canis*, and canine babesiosis caused by the protozoan parasites *Babesia canis* and *Babesia gibsoni*.

Other objects and advantages of this invention will become readily apparent from the ensuing description.

BRIEF DESCRIPTION OF THE DRAWINGS

FIG. 1A shows the amino acid sequence (SEQ ID NO: 1) of the fragment of the aquaporin protein, Contig 12018, described herein which was isolated from *R. microplus*. FIG. 1B shows the amino acid sequence (SEQ ID NO: 2) of the aquaporin protein fragment as cloned into and produced by *Pichia pastoris* expression vector pPICZalphaA as described in Guerrero et al. (U.S. Pat. No. 8,722,063 issued on May 13, 2014). The amino acids of the tick aquaporin protein are underlined (amino acids 92-290 of SEQ ID NO: 2), while extra amino acids not of tick origin but from the vector are not underlined (amino acids 1-91 and 291-317 of SEQ ID NO: 2). FIG. 1C shows the amino acid sequence (SEQ ID NO: 3) of the aquaporin protein fragment as cloned into and produced by the DNA vaccine expression vector pcDNA4mycHis C as described in Guerrero et al. The amino acids of the tick aquaporin protein are underlined (amino acids 1 and 3-198 of SEQ ID NO: 3), while substituted/extra amino acids not of tick origin are not underlined (amino acids 2 and 199-226 of SEQ ID NO: 3). Although the substituted/extra amino acids are not of tick origin, they are present in the structure of the final protein product used in the vaccine in the Example.

FIG. 2A shows the nucleotide sequence (SEQ ID NO: 5) of the cDNA from *R. microplus* encoding the isolated aquaporin protein fragment of FIG. 1A and includes an untranslated 5' region. The translated region coding for the isolated aquaporin protein fragment of FIG. 1A is underlined and corresponds to nucleotides 348-947 of the sequence. FIG. 2B shows the aquaporin nucleotide sequence (SEQ ID NO: 6) as cloned into *P. pastoris* expression vector pPICZalphaA as described in Guerrero et al. The underlined sequence (nucleotides 274-870) corresponds to the nucleotide sequence of the coding region of FIG. 2A above except that the three 3' terminal nucleotides have been removed. The nucleotide sequence shown includes extra, optional vector-provided nucleotides (nucleotides 1-273 and 871-954, not underlined) which code for the extra amino acids not of tick origin. FIG. 2C shows the aquaporin nucleotide sequence (SEQ ID NO: 7) as cloned into the DNA expression vector pcDNA4mycHis C as described in Guerrero et al. The underlined sequence (nucleotides 4-598) corresponds to the nucleotide sequence of the coding region of FIG. 2A above except that the second codon triplet has been changed from AAG to GAG, and the five 3' terminal nucleotides have been removed. The nucleotide sequence shown includes extra, optional DNA vaccine expression vector-provided nucleotides (1-3 and 599-684, not underlined) of which the 5' terminal nucleotides code for the extra amino acids not of tick origin. The nucleotide sequence corresponding to nucleotides 4-598 of SEQ ID NO: 7 is also presented as SEQ ID NO: 8 (wherein the extra nucleotides from the DNA vaccine expression vector are not included).

FIG. 3 shows a nucleotide sequence (SEQ ID NO: 9) encoding the isolated aquaporin protein fragment of FIG. 1A wherein the translated or coding region of the nucleotide sequence of FIG. 2A (nucleotides 348-942) has been optimized to enhance translation in *P. pastoris*.

DEFINITIONS

Figure 4:
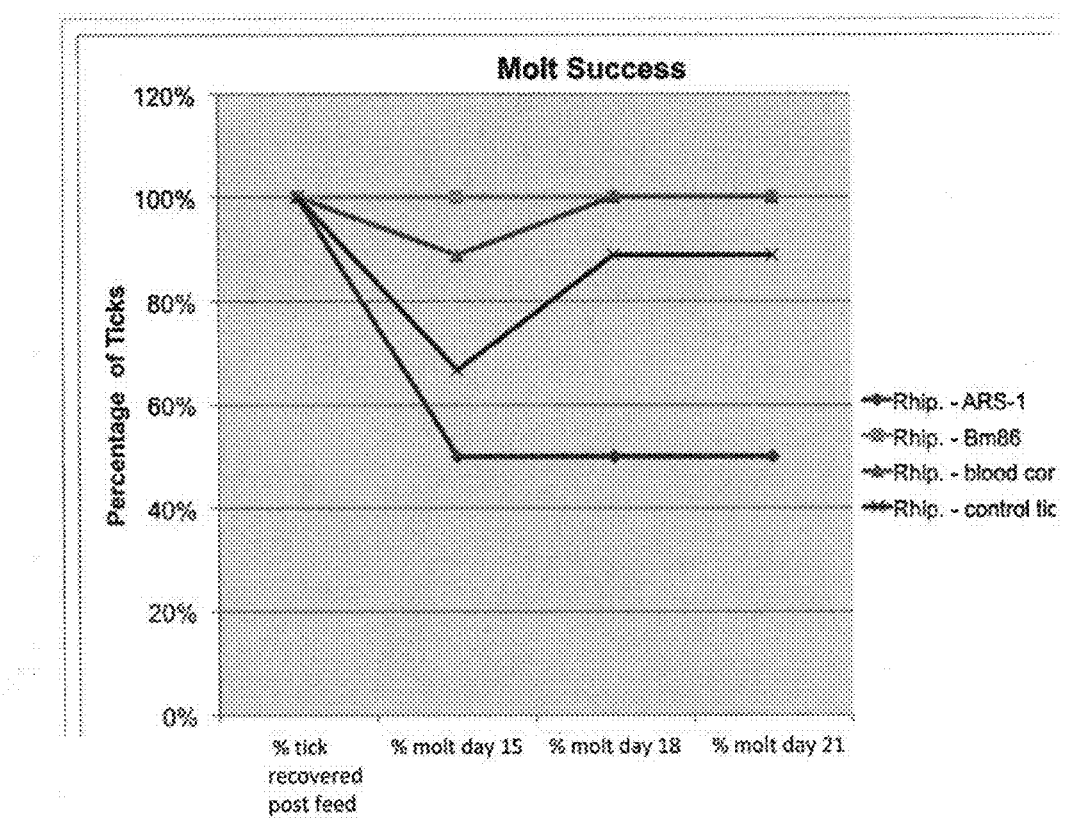
FIG. 4 shows the molting success of *R. sanguineus* ticks capillary fed pooled blood treatments as described in Example 1.

The following terms are employed herein:

Cloning. The selection and propagation of (a) genetic material from a single individual, (b) a vector containing one gene or gene fragment, or (c) a single organism containing one such gene or gene fragment.

Cloning Vector. A plasmid, virus, retrovirus, bacteriophage or nucleic acid sequence which is able to replicate in a host cell, characterized by one or a small number of restriction endonuclease recognition sites at which the sequence may be cut in a predetermined fashion, and which contains a marker suitable for use in the identification of transformed cells, e.g., uracil utilization, tetracycline resistance, ampicillin resistance. A cloning vector may or may not possess the features necessary for it to operate as an expression vector.

Codon. A DNA sequence of three nucleotides (a triplet) which codes (through mRNA) for an amino acid, a translational start signal, or a translational termination signal. For example, the nucleotide triplets TTA, TTG, CTT, CTC, CTA, and CTG encode for the amino acid leucine, while TAG, TAA, and TGA are translational stop signals, and ATG is a translational start signal.

Complement or Complementary Sequence. The product of complementary base pairing in which purines bond with pyrimidines, as it occurs in the two polynucleotide chains of DNA (adenine with thymine, guanine with cytosine) and between DNA and messenger RNA nucleotides during transcription.

DNA Coding Sequence. A DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, prokaryotic sequences and cDNA from eukaryotic mRNA. A polyadenylation signal and transcription termination sequence will usually be located 3' to the coding sequence.

DNA Sequence. A linear series of nucleotides connected one to the other by phosphodiester bonds between the 3' and 5' carbons of adjacent pentoses.

Expression. The process undergone by a structural gene to produce a polypeptide. Expression requires both transcription of DNA and translation of RNA.

Expression Vector. A replicon such as a plasmid, virus, retrovirus, bacteriophage, or nucleic acid sequence which is able to replicate in a host cell, characterized by a restriction endonuclease recognition site at which the sequence may be cut in a predetermined fashion for the insertion of a heterologous DNA sequence. An expression vector has a promoter positioned upstream of the site at which the sequence is cut for the insertion of the heterologous DNA sequence, the recognition site being selected so that the promoter will be operatively associated with the heterologous DNA sequence. A heterologous DNA sequence is "operatively associated" with the promoter in a cell when RNA polymerase, which binds the promoter sequence transcribes the coding sequence into mRNA which is then in turn translated into the protein encoded by the coding sequence.

Fusion Protein. A protein produced when two heterologous genes or fragments thereof coding for two different proteins not found fused together in nature are fused together in an expression vector. For the fusion protein to correspond to the separate proteins, the separate DNA sequences must be fused together in correct translational reading frame.

Gene. A segment of DNA which encodes a specific protein or polypeptide, or RNA.

Genome. The entire DNA of an organism. It includes, among other things, the structural genes encoding for the polypeptides of the substance, as well as operator, promoter and ribosome binding and interaction sequences.

Heterologous DNA. A DNA sequence inserted within or connected to another DNA sequence which codes for polypeptides not coded for in nature by the DNA sequence to which it is joined. Allelic variations or naturally occurring mutational events do not give rise to a heterologous DNA sequence as defined herein.

Hybridization. The pairing together or annealing of single stranded regions of nucleic acids to form double-stranded molecules.

Nucleotide. A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C"), and thymine ("T"). The four RNA bases are A, G, C, and uracil ("U").

Phage or Bacteriophage. Bacterial virus many of which include DNA sequences encapsidated in a protein envelope or coat ("capsid"). In a unicellular organism, a phage may be introduced by a process called transfection.

Plasmid. A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. A cell transformed by a plasmid is called a "transformant".

Polypeptide. A linear series of amino acids connected one to the other by peptide bonds between the alpha-amino and carboxy groups of adjacent amino acids.

Promoter. A DNA sequence within a larger DNA sequence defining a site to which RNA polymerase may bind and initiate transcription.

Reading Frame. The grouping of codons during translation of mRNA into amino acid sequences. During translation the proper reading frame must be maintained. For example, the DNA sequence may be translated via mRNA into three reading frames, each of which affords a different amino acid sequence.

Recombinant DNA Molecule. A hybrid DNA sequence comprising at least two DNA sequences, the first sequence not normally being found together in nature with the second.

Ribosomal Binding Site. A nucleotide sequence of mRNA, coded for by a DNA sequence, to which ribosomes bind so that translation may be initiated. A ribosomal binding site is required for efficient translation to occur. The DNA sequence coding for a ribosomal binding site is positioned on a larger DNA sequence downstream of a promoter and upstream from a translational start sequence.

Start Codon. Also called the initiation codon, is the first mRNA triplet to be translated during protein or peptide synthesis and immediately precedes the structural gene being translated. The start codon is usually AUG, but may sometimes also be GUG.

Stringent Hybridization Conditions. The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and will differ in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length. Typically, stringent hybridization conditions comprise hybridization in 50% formamide, 1 M NaCl, 1% SDS at 42° C., and a wash in 0.1×SSC at 60 to 65° C. It is also understood that due to the advances in DNA PCR and sequencing approaches that issues of gene identity and homology may be determined by sequence based rather than hybridization approaches.

Structural Gene. A DNA sequence which encodes through its template or messenger RNA (mRNA) a sequence of amino acids characteristic of a specific polypeptide.

Substantially Pure. The condition of a compound, such as a protein or a nucleotide, being cell free or being separated from other components that would interfere with or have a substantial qualitative effect on the activity of the compound or on a substrate on which the compound acts.

Transform. To change in a heritable manner the characteristics of a host cell in response to DNA foreign to that cell. An exogenous DNA has been introduced inside the cell wall or protoplast. Exogenous DNA may or may not be integrated (covalently linked) to chromosomal DNA making up the genome of the cell. In prokaryotes and some fungi, for example, the exogenous DNA may be maintained on an episomal element such as a plasmid. With respect to most eukaryotic cells, a stably transformed cell is one in which the exogenous DNA has been integrated into a chromosome so that it is inherited by daughter cells through chromosome replication. This stability is demonstrated by the ability of the eukaryotic cell to establish cell lines or clones comprised of a population of daughter cells containing the exogenous DNA.

Transcription. The process of producing mRNA from a structural gene.

Translation. The process of producing a polypeptide from mRNA.

Vaccine. Vaccine is defined herein in its broad sense to refer to any type of biological agent in an administrable form capable of stimulating a protective immune response in an animal inoculated with the vaccine. For purposes of this invention, the vaccine may comprise either one or more of the immunogenic (antigenic) proteins or nucleic acid constructs encoding these proteins.

DETAILED DESCRIPTION OF THE INVENTION

In the following description, the nomenclature used to define the proteins and peptides is that specified by Schroder and Lubke ["The Peptides," Academic Press (1965)] wherein, in accordance with conventional representation, the N-terminal appears to the left and the C-terminal to the right. Where the amino acid residue has isomeric forms, it is the L-form of the amino acid that is represented herein unless otherwise expressly indicated.

The immunogenic protein which is utilized herein is an aquaporin protein fragment from the cattle tick, *R. microplus*. This aquaporin protein fragment, as well as the nucleic acid sequences encoding this aquaporin protein, are described in Guerrero et al., U.S. patent application Ser. No. 13/479,486, filed May 24, 2012, the contents of which are incorporated by reference herein. Guerrero et al. also discloses that this aquaporin protein fragment, and nucleic acid constructs comprising the nucleic acid sequence encoding this aquaporin protein, may be used as vaccines to control and prevent infestations of *R. microplus* in treated livestock, including bovines. We have now discovered that the same aquaporin protein from *R. microplus*, and the nucleic acid constructs incorporating the nucleic acid sequence encoding this aquaporin protein, are not only effective for eliciting a protective immune response against the cattle tick in bovine animals, but also for eliciting a protective immune response against other tick species in other, non-bovine animals. In particular, we have discovered that the aquaporin protein or nucleic acid constructs are effective for eliciting a protective immune response against the brown dog tick, *R. sanguineus*, in a variety of animals, preferably deer (including white-tailed deer), horses, domestic dogs and cats. Moreover, without being limited thereto, it is envisioned that the aquaporin protein or nucleic acid constructs are effective for eliciting a protective immune response against other ticks, including *Ixodes holocyclus* (Australia paralysis tick), *I. ricinus, I. pacificus, I. hexagonus, I. canisuga, Rhipicephalus turanicus, Dermacentor variabilis* (American dog tick), *D. andersoni, D. reticulates, Amblyomma americanum* (Lone star tick), *A. maculatum* and *Otobius megnini*.

The aquaporin protein fragment of the cattle tick, *R. microplus*, has been isolated, substantially free from other proteins or cell components which are normally present in the cells of the tick, such that the aquaporin protein is the only significant protein or peptide in the sample and may be used effectively as a vaccine. Moreover, the protein has been produced in recombinant form as described in Guerrero et al. and herein below. The term "isolated" encompasses not only proteins which have been recovered from naturally occurring cells, but also recombinant proteins and synthesized proteins. The aquaporin protein fragments, including recombinants, are immunogenic, effective for eliciting a protective immune response against ticks other than the cattle tick, which response is mediated by humoral, i.e., antibodies, and/or cellular processes.

The isolated aquaporin protein fragment of R. microplus has been sequenced, and its amino acid sequence is shown in FIG. 1A. The amino acid sequence of the isolated aquaporin protein fragment corresponds to SEQ ID NO: 1. The isolated aquaporin protein fragment has a calculated molecular weight of 21.2 kDa based on the amino acid sequence. Moreover, when utilizing recombinant proteins, the aquaporin protein fragment may be modified to assist cloning in the selected vector, and the expressed protein may further include optional, additional terminal amino acid sequences from the vector (not of tick origin). For example, FIG. 1B shows the amino acid sequence (SEQ ID NO: 2) of the aquaporin protein fragment as cloned into and produced by the Pichia pastoris expression vector pPICZalphaA as described in Guerrero et al. The underlined sequence of FIG. 1B corresponds to the amino acid sequence of FIG. 1A, except that the C-terminal amino acid (L) of the isolated fragment has been removed to assist cloning of the aquaporin gene into the plasmid. The amino acid sequence also includes extra, optional amino acids from the cloning vector. The amino acids of the tick aquaporin protein are underlined (amino acids 92-290 of SEQ ID NO: 2), while the extra amino acids not of tick origin are not underlined (amino acids 1-91 and 291-317 of SEQ ID NO: 2). FIG. 1C shows the amino acid sequence (SEQ ID NO: 3) of the aquaporin protein fragment as cloned into and produced by the DNA vaccine expression vector pcDNA4mycHis C also as described in Guerrero et al. The underlined sequence corresponds to the amino acid sequence of FIG. 1A above, except that amino acid 2 has been changed (from K to E) and the two C-terminal amino acids (PL) of the isolated fragment have been removed to assist cloning of the aquaporin gene into the plasmid. Thus, amino acids 3-198 of SEQ ID NO: 1 are common to each of the aquaporin sequences of FIGS. 1A, B and C. The amino acid sequence of FIG. 1C also includes optional amino acids from the DNA vaccine expression vector. The amino acids of the tick aquaporin protein are underlined (amino acids 1 and 3-198 of SEQ ID NO: 3), while the changed/extra amino acids not of tick origin are not underlined (amino acids 2 and 199-226 of SEQ ID NO: 3). The amino acid sequence corresponding solely to amino acids 1-198 of SEQ ID NO: 3 is also presented as SEQ ID NO: 4 (the extra amino acids from the DNA vaccine expression vector are not included).

It is envisioned that the R. microplus aquaporin protein may be synthesized by any suitable method well known to those skilled in the art of peptide synthesis, such as exclusively solid-phase techniques, partial solid-phase techniques, fragment condensation, or classical solution addition. For example, without being limited thereto, suitable solution phase synthesis methods are described by Finn and Hoffman [In "Proteins," Vol. 2, 3rd Ed., H. Neurath and R. L. Hill (eds.), Academic Press, New York, pp. 105-253 (1976)], while solid phase synthesis methods are described by Barany and Merrifield [In "The Peptides," Vol. 2, E. Gross and J. Meienhofer (eds.), Academic Press, New York, pp. 3-284 (1979)], and stepwise solid phase synthesis methods are described by Merrifield [J. Am. Chem. Soc. 85: 2149-2154 (1963)], the contents of each of which are incorporated herein by reference. However, the protein is preferably produced by recombinant DNA techniques which are particularly suitable for large-scale use. Without being limited thereto, nucleotide sequences encoding the protein which are preferred for use in recombinant DNA techniques are described in detail below. The synthetic protein may be obtained by transforming a microorganism using an expression vector including a promoter or operator, or both, together with the aquaporin structural gene and causing such transformed microorganisms to express the protein.

The gene encoding the aquaporin protein fragment of R. microplus has also been isolated and its cDNA nucleic acid sequences is shown in FIG. 2A. The nucleic acid sequence of the translated region of the cDNA encoding the aquaporin protein fragment corresponds to nucleotides 348-947 of SEQ ID NO: 5. FIG. 2A also includes an untranslated 5' region (not underlined). As used herein, isolated nucleic acid sequences refer to sequences which have been substantially separated from other nucleic acids or cell components which are normally present in the cells of the tick, such that the aquaporin encoding sequences are the only significant sequences in the sample that can be used to express or produce the protein in a host cell as described below. The term encompasses not only nucleic acid sequences which have been recovered from naturally occurring cells, but also recombinant or cloned nucleic acid sequences, and synthesized nucleic acid sequences. The nucleic acid sequences may be recovered from cells of R. microplus, for example, by constructing a genomic DNA or cDNA library and screening for the aquaporin protein nucleic acid using the disclosed sequences as probes. However, in a preferred embodiment, the sequences are synthesized using techniques established in the art for automated DNA synthesis or amplification. As used herein, the nucleic acid sequences of the aquaporin protein encompass either or both of the coding strand or its complement.

As noted above, the amino acid sequence of the aquaporin protein fragment may be modified to assist cloning in the selected vector, and may further include optional, additional terminal amino acid sequences from the vector (not of tick origin). Thus, the nucleic acid sequence may be modified to reflect these changes. For example, FIG. 2B shows the aquaporin nucleotide sequence (SEQ ID NO: 6) as cloned into the P. pastoris expression vector pPICZalphaA as described in Guerrero et al. The underlined sequence of FIG. 2B (nucleotides 274-870) corresponds to the nucleotide sequence of the coding region of FIG. 2A above except that the three 3' terminal nucleotides (nucleotides 945-947 of FIG. 2A) have been removed to assist cloning of the gene into the plasmid. The nucleotide sequence shown includes extra, optional vector-provided nucleotides (nucleotides 1-273 and 871-954, not underlined) which code for the extra amino acids not of tick origin (amino acids 1-91 and 291-317 of SEQ ID NO: 2). FIG. 2C shows the aquaporin nucleotide sequence (SEQ ID NO: 7) as cloned into the DNA expression vector pcDNA4mycHis C as described in Guerrero et al. The underlined sequence (nucleotides 4-598) corresponds to the nucleotide sequence of the coding region of FIG. 2A above except that the second codon triplet (nucleotides 351-353 of FIG. 2A) has been changed from AAG to GAG, and the five 3' terminal nucleotides (nucleotides 943-947 of FIG. 2A) have been removed, to assist cloning of the gene into the plasmid and enhance translation. Thus, nucleotides 354-942 of SEQ ID NO:5 are common to each of the aquaporin coding sequences of FIGS. 2A, B and C. The nucleotide sequence shown includes extra, optional DNA vaccine expression vector-provided nucleotides on both of the 3' and 5' ends (1-3 and 599-684, not underlined) of which the 3' terminal nucleotides code for the extra amino acids not of tick origin (amino acids 200-226 of SEQ ID NO: 2). The nucleotide sequence corresponding to nucleotides 4-598 of SEQ ID NO: 7 is also presented as SEQ ID NO: 8 (wherein the extra nucleotides from the DNA vaccine expression vector are not included). In addition, because of the degeneracy of the genetic code, there exists a finite set of nucleotide sequences which can code for a given amino acid sequence. Consequently, nucleic acids may be identical in sequence to the sequence which is naturally occurring or they may include alternative codons which encode the same amino acid as that which is found in the naturally occurring sequence. Furthermore, nucleic acids may include codons which represent conservative substitutions of amino acids as are well known in the art. Moreover, because of the degeneracy of the genetic code, different species can preferentially use different codons to code for the same amino acid and significant differences in tRNA abundance can exist. Translation of recombinant proteins can often be enhanced by optimizing codon usage to the preferred codons used by the expression species. For example, in the yeast *P. pastoris* the amino acid arginine is encoded by the nucleotide triplet of AGA approximately 10 times more frequently than by the nucleotide triplet of CGG. Substitution of CGG triplets with AGA in a *R. microplus* protein coding region used in a recombinant *P. pastoris* expression system would be expected to enhance recombinant protein expression levels. It is understood that all such equivalent sequences are operable variants of the disclosed sequences, since all give rise to the same aquaporin protein (i.e., the same amino acid sequence) during in vivo transcription and translation, and are hence encompassed herein. Without being limited thereto, examples of codon-optimized sequences which would be suitable for enhancing translation of the aquaporin protein fragment in *P. pastoris* are shown in FIG. 3. The sequence of FIG. 3 (SEQ ID NO: 9) corresponds to the translated or coding region of the nucleotide sequence of FIG. 2A (nucleotides 348-942) which has been optimized to enhance translation in *P. pastoris*. DNA sequences which contain significant sequence similarity to the coding regions of the nucleotide sequence of SEQ ID NO: 5 are also encompassed by the invention. As defined herein, two DNA sequences contain significant sequence similarity when at least 85% (preferably at least 90% and most preferably 95%) of the nucleotides match over the defined length of the sequence. Sequences that are significantly similar can be identified in a Southern hybridization experiment under stringent hybridization conditions as is known in the art. See, for example, Sambrook et al., Molecular Cloning: A Laboratory Manual (2$^{nd}$ Ed.), Vol. 1-3, Cold Spring Harbor Laboratory, Cold Spring Harbor, N.Y., 1989, or DNA Cloning: A Practical Approach, Vol. I and II (Ed. D. N. Glover), IRL Press, Oxford, 1985.

Any one or combinations of the isolated cDNA nucleic acid sequences encoding the *R. microplus* aquaporin protein may be cloned into any suitable vector for subsequent use as either a DNA vaccine or for the production of recombinant *R. microplus* aquaporin protein. For use as a DNA vaccine, the nucleic acid constructs comprising the nucleic acid sequences encoding the *R. microplus* aquaporin protein are administered to a subject animal such that the protein is expressed in vivo within the cells of the vaccinated animal. Similarly, where the object is the production of recombinant protein, the nucleic acid constructs are used for the transformation of a microorganism and causing such transformed microorganism to express the protein in vitro.

A variety of vectors are suitable for use herein, and are selected to be operable as cloning vectors or expression vectors in the selected host cell, although expression vectors are preferred. Numerous vectors are known to practitioners skilled in the art, and selection of an appropriate vector and host cell is a matter of choice. The vectors may, for example, be bacteriophage, plasmids (including linearized or circular plasmids), viruses or hybrids thereof, such as those described in Sambrook et al. (ibid) or Ausubel et al. (Current Protocols in Molecular Biology, John Wiley & Sons, Inc, 1995), the contents of each of which are herein incorporated by reference. Further, the vectors may be non-fusion vectors (i.e., those producing the proteins of the invention not fused to any heterologous polypeptide), or alternatively, fusion vectors (i.e., those producing the proteins fused to a vector encoded polypeptide). The fusion proteins would of course vary with the particular vector chosen. In accordance with a preferred embodiment, and particularly for applications as DNA vaccines, the vectors are eukaryotic expression vectors, most preferably plasmids. Particularly preferred plasmids for use herein include plasmids commercially available from Invitrogen Inc., Carlsbad, Calif. for both the DNA vaccine and recombinant protein vaccine protocols. The pcDNA 4/myc 5.1 kb vectors are designed for overproduction of recombinant proteins in mammalian cells. This plasmid contains a human cytomegalovirus immediate-early (CMV) promoter for high-level expression, a c-myc epitope and 6×His metal-binding peptide tag for facilitating protein purification and verification, and a Zeocin antibiotic resistance marker gene coding region for selection purposes. The preferred plasmids used to produce recombinant protein are the pPICZ and pPICZα from Invitrogen Inc. Both plasmids contain the AOX1 gene promoter for methanol-inducible high-level expression in *Pichia pastoris*, a c-myc epitope and 6×His metal-binding peptide tag for facilitating protein purification and verification, and a Zeocin antibiotic resistance marker gene coding region for selection purposes. The pPICZα also contains a native *Saccharomyces cerevisiae* α-factor secretion signal.

Regardless of the specific vector utilized, various sites may be selected for insertion of the isolated nucleotide sequences. These sites are usually designated by the restriction enzyme or endonuclease that cuts them.

The particular site chosen for insertion of the selected nucleotide sequences into the vector to form a recombinant vector is determined by a variety of factors. These include size and structure of the protein to be expressed, susceptibility of the desired protein to enzymatic degradation by the host cell components and contamination by its proteins, expression characteristics such as the location of start and stop codons, and other factors recognized by those skilled in the art. None of these factors alone absolutely controls the choice of insertion site for a particular polypeptide. Rather, the site chosen reflects a balance of these factors, and not all sites may be equally effective for a given protein.

The nucleotide sequences comprising the *R. microplus* aquaporin protein fragment encoding gene may be inserted into the desired vector by known techniques. If, however, the vector is to serve as an expression vector, the vector should have a promoter effective for expression in the selected host cell, and the DNA sequences should be inserted in the vector downstream of the promoter and operationally associated therewith (that is, the promoter should be recognized by the RNA polymerase of the host cell). In addition, the vector should have a region which codes for a ribosome binding site positioned between the promoter and the site at which the DNA sequence is inserted so as to be operatively associated with the DNA sequence of the invention once inserted (in correct translational reading frame therewith). The vector should be selected to provide a region which codes for a ribosomal binding site recognized by the ribosomes of the host cell into which the vector is to be inserted. The vector should contain a terminator with necessary 3' untranslated sequences for RNA termination, stability, and/or poly(A) tail addition (if eukaryotic). Alternatively, any or all of the above control sequences may be ligated to the coding sequence prior to insertion into the vector.

For use in animal vaccinations, the isolated R. microplus aquaporin protein fragment or the nucleic acid constructs comprising the nucleic acid sequences encoding this protein, will typically be formulated in conjunction with a suitable pharmaceutically acceptable carrier or diluent as is known in the art, including, but not limited to, physiological saline, mineral oil, vegetable oils, aqueous carboxymethyl cellulose or polyvinylpyrrolidone. The skilled practitioner will recognize that such carriers should of course be compatible with the protein or nucleic acid constructs. Phosphate buffered saline (PBS) is preferred. Because aquaporin may precipitate in the presence of aqueous buffers such as PBS, in a preferred embodiment the aquaporin is stored in a non-polar solvent or oil. A variety of non-polar solvents are suitable for use herein, although a preferred solvent is composed of 50 mM NaH2PO4, pH 8.0, 300 mM NaCl, 2 mM beta-mercaptoethanol, 0.4% w/v OTG (octyl-beta-D-1-thioglucopyranoside), 300 mM imidazole, and 50% glycerol. The concentration and amount of the protein or nucleic acid constructs in the final composition may vary depending upon the desired use and type of response needed, and the host animal. In any event, the protein or nucleic acid constructs should be provided in an amount effective to induce the preferred response as determined by routine testing. Appropriate adjuvants as known in the art may also be included in the formulation. As described herein, adjuvants include agents (a compound or combination of compounds) capable of enhancing either or both of a humoral (antibody) immunity response or a cell-mediated immunity response in the treated animal against the target tick. Without being limited thereto, suitable adjuvants include but are not limited to one or more of mineral oil, vegetable oils, aluminum salts such as alum, water-in-oil adjuvants such as Freund's incomplete adjuvant, oil-in-water emulsions such as MF59 (Novartis, Switzerland), liposomes, virosomes, microparticles or nanoparticles or beads of biocompatible matrix materials such as (although not limited to) agar or polyacrylate, saponin-based adjuvants (such as QA-21 or QS-21 marketed by Antigenics, Lexington, Mass.), toll-like receptor (TLR) agonists such as 3-O-desacyl-4'-monophosphoryl lipid A (MPL) and immunostimulatory sequences (ISS) of microbial DNA, imidazoquinolines, immune stimulating complexes (ISCOMs and ISCOMATRIXs), and other agents such as described by Leroux-Roels (2010. Vaccine. 285:C25-C36, the contents of which are incorporated by reference herein). In accordance with an optional embodiment, other known immunogenic agents used in conventional vaccines for the animal of interest may also be included in the formulation. For example, additional immunogenic agents may be an attenuated or inactivated form of a pathogen, or subunits thereof. Without being limited thereto, these pathogens include, for example, one or more of the rabies virus, *Borrelia burgdorferi*, canine distemper virus, canine parvovirus, canine adenovirus, canine corona virus, canine herpesvirus, *Giardia* spp., *Leptospira interrogans, Babesia canis, Hepatozoon canis, Dipylidium caninum* and *Isospora* spp.

The immunogenic R. microplus aquaporin protein fragment or the nucleic acid constructs comprising the nucleic acid sequences encoding this protein are administered in an amount effective to reduce or eliminate the incidence of infestation of the treated animal, with the specific target tick, particularly but not limited to the brown dog tick, R. sanguineus. As noted hereinabove, the administration of the R. microplus aquaporin protein, or the nucleic acid constructs comprising the nucleic acid sequences encoding this protein (such that the nucleic acid sequences are expressed and the encoded protein is produced in vivo in the cells of the vaccinated animal), stimulates an immune response in the animal. Thus, as used herein, an "effective amount" of R. microplus aquaporin protein or the nucleic acid constructs comprising the nucleic acid sequences encoding this protein, is preferably defined as that amount which will elicit a protective immune response against the target tick, which may be either or both of antibody production against the protein or a cell-mediated immune response against the tick, in a treated animal in comparison to an untreated control animal. In a preferred embodiment, an immune response may be demonstrated by production of antibodies against the R. microplus aquaporin protein, by a significant reduction in the percentage of animals infested with the target tick, by a significant reduction in the average number of target ticks on animals, or by a significant reduction in the number of viable eggs produced by the target ticks present on animals, all in vaccinated animals as compared to an unvaccinated control group (measured at a confidence level of at least 80%, preferably measured at a confidence level of 95%). The actual effective amount will of course vary with the specific vaccine component (protein vaccine or DNA vaccine), the particular animal of interest and its age and size, and the route of administration, and may be readily determined empirically by the practitioner skilled in the art using an antigen dose response assay. By way of example and without being limited thereto, for vaccines administered to small animals (such as dogs and cats) by subcutaneous or intramuscular injection, or with a needleless device, it is envisioned that typical doses of protein vaccine (R. microplus aquaporin protein), may be greater than 0.3 µg protein/animal/dose, preferably between about 0.3 to 1.75 µg protein/animal/dose, while typical doses of DNA vaccine (nucleic acid constructs) may be greater than 100 µg of DNA construct/animal/dose, preferably between about 300 to 800 µg DNA construct/animal/dose. For vaccines administered to large animals (such as deer and horses) by subcutaneous or intramuscular injection, or with a needleless device, it is envisioned that typical doses of protein vaccine (R. microplus aquaporin protein), may be greater than 10 µg protein/animal/dose, preferably between about 50 to 150 µg protein/animal/dose, while typical doses of DNA vaccine (nucleic acid constructs) may be greater than 100 µg of DNA construct/animal/dose, preferably between about 300 to 800 µg DNA construct/animal/dose.

The vaccines (R. microplus aquaporin protein or the nucleic acid constructs comprising the nucleic acid sequences encoding this protein) may be used for the treatment of a broad spectrum of wild or domesticated animals, ranging from pets and companion animals to livestock and large domestic or wild animals. Without being limited thereto, the vaccines are preferably used for the treatment of Cervidae, equine, canines and felines, and particularly deer (including white-tailed deer), horses, domestic dogs and cats. The vaccines may be effectively administered any time after the animal attains immunocompetence. The vaccines may be administered to the subject animal by any convenient route which enables an immune response. However, parenteral injection (e.g., subcutaneous, intravenous, or intramuscular) is preferred, with intradermal injection being particularly preferred for administration of the DNA vaccines and intramuscular injection being particularly preferred for administration of the protein vaccines. The vaccine products could also be administered using a needle-less device. The vaccine may be administered in a single dose or in a plurality of doses. Dependent upon rearing conditions, the vaccine may be administered in multiple doses, the timing of which may be readily determined by the skilled artisan.

Where the nucleic acid constructs are to be employed for the production of recombinant R. microplus aquaporin protein, a variety of vector-host cell expression systems may be employed. Strains of yeast, particularly Pichia pastoris, are preferred. However, the novel invention described here can be applied with numerous host cells that would desirable. Host strains may be of bacterial, fungal, insect cell line, plant, or yeast origin. Ascertaining the most appropriate host-vector system is within the skill of the person in the art.

DNA constructs may be introduced into the appropriate host cell by numerous methods described in the technical and scientific literature. Transformation of bacteria or yeast may be performed using standard techniques described in Sambrook et al., (ibid). Techniques for transforming filamentous fungi may include those described by Goosen et al. [Handbook for Applied Mycology, Arora, Elander & Mukerji, eds. (1992) pp. 151-195] and May et al. [Applied Molecular Genetics of Filamentous Fungi, Kinghorn and Turner, eds. (1992) pp. 1-27]. In general, linear or circular DNA constructs may be introduced into the host cell by techniques utilizing protoplast fusion, polyethylene glycol, liposomes, lithium acetate, electroporation, physical damage, biolistic bombardment, or Agrobacterium mediated transformation.

Successful transformants may be isolated by using markers, contained on the expression vectors, which confer a selectable trait to the transformed host cell. These may include nutritional selection related to substrate utilization (such as, growth on acetamide containing medium) or prototrophy of a required growth product (such as, arginine, leucine, or uracil). Dominant selectable markers [such as, resistance to ampicillin, G418, hygromycin, and phleomycin, and Zeocin (a composition of bleomycin and phleomycin, Invitrogen, Grand Island, N.Y.)] are also useful in selecting transformants that have taken up the introduced DNA construct.

The DNA construct may be replicated autonomously or integrated into the genome of the host cell. Integration typically occurs by homologous recombination (for example, arginine selectable marker integrating in the chromosomal arginine gene) or at a chromosomal site unrelated to any genes on the DNA construct. Integration may occur by either a single or double cross-over event. It is also possible to have any number of these integration and replication types occurring in the same transformant.

The following example is intended only to further illustrate the invention and is not intended to limit the scope of the invention which is defined by the claims.

Example 1

Recombinant aquaporin protein fragment of R. microplus was prepared as described in Example 1 of Guerrero et al. (U.S. patent application Ser. No. 13/479,486, referred to above). Prior to use, the recombinant aquaporin protein was stored in a phosphate buffered solution composed of 50 mM NaH2PO4, pH 8.0, 300 mM NaCl, 2 mM beta-mercaptoethanol, 0.4% w/v OTG (octyl-beta-D-1-thioglucopyranoside), 300 mM imidazole, and 50% glycerol. Recombinant Bm86Texas antigenic protein of R. (Boophilus) microplus was obtained from cloning of the protein antigen Bm86 from a Texas outbreak strain of R. microplus known as Deutsch. Recombinant aquaporin protein and Bm86Texas antigens were each adjuvated with Montanide ISA 61 VG (water-in-oil adjuvant, Seppic, Paris) into doses of 2 ml containing 100 ug of the recombinant protein.

Three groups of tick-naive white-tailed deer (n=4 per group) received 1.0 mL of either the recombinant aquaporin protein vaccine, Bm86 vaccine, or a control vaccine at week 1. Deer were housed at the LSU Idelwild Research Station in Clinton, La. Each deer was vaccinated on day 1, and blood was collected from each animal at the intervals shown in Table 1. The blood from the Week 3 collections from the control, aquaporin and Bm86Texas groups was used to prepare serum and feed to ticks in the following in vitro study. Individual blood samples within treatment groups were pooled in the tick feeding trials.

Four groups of R. sanguineus ticks (n=10 nymphs per group) were partially-fed on rats for 2 days prior to the treatment feeding with blood from the blood samples collected from the deer. Experimental groups were fed from 50 μL glass microcapillary tubes containing the pooled blood treatments. The control tick group only fed from the rats. Nymphs were subsequently fed to repletion on rats. Nymphs were placed in environmental chambers at 26° C. at 92% humidity and monitored for molting success up to 21 days post feeding to repletion. Tick groups were less than n=10 at the time of chamber placement. Deaths due to handling techniques were experienced in each group and additional deaths also occurred within 48 hours of feeding the vaccinated blood. Groups were decreased to the following sizes: aquaporin (n=6), Bm86 (N=7), vaccinated control (n=9), and tick control (n=9).

The data for tick molting success was analyzed using an exact probability chi-square test; there were significant differences in the molting success of the four groups (p=0.0255) with the majority of the significance associated with the ARS-1 group having more dead than expected. The results are shown in FIG. 4. Only 50% of the ticks fed with blood of deer vaccinated with aquaporin protein survived the molting process. This is compared to the Bm86 and blood control vaccinated groups which both had a molting/survival rate of 100%. The tick control group had a 90% molting/survival rate (FIG. 4).

Blood from the deer was also sampled at the intervals shown in Table 1 and separated serum was collected for analysis by ELISA to determine antibody production in vaccinated deer to the aquaporin protein or the BM86 antigens. For the ELISA, sera from each group were pooled according to the day of collection. Microtiter plates were coated with the aquaporin protein or the Bm86 antigen (50 μL per well of a 1 μg antigen/ml solution in 20 mM sodium carbonate buffer, pH 9.6) and incubated overnight at 4° C. Blocking with 2% bovine serum albumin in PBS-T was followed by washing five times with PBS pH 7.4. The plates were incubated for 45 min at 37° C. with 100 μL per well of immunized bovine serum diluted to 1:100 in PBS. After washing, 50 μl of rabbit anti-bovine IgG peroxidase conjugate (Sigma, St. Louis, Mo.) diluted to 1:20,000 was added and the plate incubated for 30 min at room temperature. After incubation and washing 50 μl of chromogenic substrate o-phenylenediamine (1.0 mM) was added and the reaction was stopped after 15 min by adding 50 μl of NaOH (0.2 M). A microplate reader was used to assess the results with absorbance set at 490 nm. The results are shown in Table 1 and demonstrate antibody production specific to the antigens.

It is understood that the foregoing detailed description is given merely by way of illustration and that modifications and variations may be made therein without departing from the spirit and scope of the invention.

TABLE 1

| Deer ID | PreVaccine | Week 3 | Week 6 | Week 10 | Week 14 | Week 18 | Week 22 |
|---|---|---|---|---|---|---|---|
| *Unvaccinated Control Group Vaccinated on day 1, Week 3 and Week 6 with only adjuvant* | | | | | | | |
| W-19 | <50 | <50 | <50 | <50 | <50 | <50 | <50 |
| 55 | 50 | <50 | <50 | <50 | died | died | died |
| 57 | <50 | <50 | <50 | <50 | <50 | 100 | <50 |
| 59 | <50 | <50 | <50 | <50 | <50 | <50 | <50 |
| *Aquaporin Group Vaccinated on day 1, Week 3 and Week 6 with Aquaporin plus adjuvant* | | | | | | | |
| 75 | 50 | 800 | 6400 | 3200 | 400 | 800 | 200 |
| 76 | 100 | 800 | >6400 | >6400 | 6400 | 6400 | 3200 |
| 78 | <50 | 6400 | 1600 | 3200 | 400 | 1600 | 400 |
| 85 | <50 | 800 | 6400 | 6400 | 1600 | 3200 | 3200 |
| *Bm86Texas antigen Group Vaccinated on day 1, Week 3 and Week 6 with Bm86Texas plus adjuvant.* | | | | | | | |
| 88 | <50 | 6400 | 800 | 3200 | 1600 | 3200 | 1600 |
| 90 | <50 | 200 | 3200 | 6400 | 1600 | 1200 | 400 |
| 91 | <50 | 1600 | 1600 | 6400 | 1600 | 1200 | 400 |
| W-94 | <50 | 800 | 400 | 1600 | 100 | 200 | 200 |

---

We claim:

1. A method of reducing *Rhipicephalus sanguineus* tick infestations in an animal comprising administering a vaccine composition to said animal, wherein said vaccine composition comprises an aquaporin protein of *Rhipicephalus microplus* and a pharmaceutically acceptable carrier, and wherein said aquaporin protein is in an amount effective to stimulate an immune response in said animal to said *Rhipicephalus sanguineus* tick, and wherein said aquaporin protein comprises at least amino acids 3-198 of SEQ ID NO: 1, wherein said animal is selected from the group consisting of canine, feline, and Cervidae.

2. The method of claim 1 wherein said aquaporin protein comprises an amino acid sequence selected from the group consisting of SEQ ID NO: 1 and SEQ ID NO: 4.

3. The method of claim 1 wherein said animal is selected from the group consisting of domestic cats, domestic dogs and deer.

4. The method of claim 3 wherein said animal is a domestic dog.

5. The method of claim 1 wherein said vaccine composition further comprises an adjuvant.

6. A method of reducing *Rhipicephalus sanguineus* tick infestations in an animal comprising administrating a vaccine composition to said animal, wherein said vaccine composition comprises a pharmaceutically acceptable carrier and a fusion protein comprising a fragment of an aquaporin protein of *Rhipicephalus microplus*, and wherein said fusion protein is in an amount effective to stimulate an immune response in said animal to said *Rhipicephalus sanguineus* tick, and wherein said fragment of said aquaporin protein comprises at least amino acids 3-198 of SEQ ID NO: 1, wherein said animal is selected from the group consisting of canines, felines, and Cervidae.

7. The method of claim 6, wherein said fusion protein comprises an amino acid sequence selected from the group consisting of SEQ ID NO: 2 and SEQ ID NO: 3.

8. The method of claim 6 wherein said animal is selected from the group consisting of domestic cats, domestic dogs and deer.

9. The method of claim 8 wherein said animal is a domestic dog.

10. The method of claim 6 wherein said vaccine composition further comprises an adjuvant.

* * * * *

SEQUENCE LISTING

<160> NUMBER OF SEQ ID NOS: 9

<210> SEQ ID NO 1
<211> LENGTH: 200
<212> TYPE: PRT
<213> ORGANISM: Rhipicephalus microplus

<400> SEQUENCE: 1

```
Met Lys Ile Glu Asn Leu Leu Ile Arg Gln Leu Ile Asn Glu Phe Leu
1               5                  10                  15

Gly Thr Met Ile Leu Ile Thr Ile Gly Asp Ser Ile Met Ala Ile Ile
            20                  25                  30

Ile Ala Gly Asp Asn Glu Ser Leu Ala Ala Cys Val Gly Pro Leu Gly
        35                  40                  45

Trp Gly Val Ala Ile Tyr Val Ala Val Gln Ile Ser Gly Gly Val Ser
    50                  55                  60

Ser His Leu Asn Pro Ala Val Thr Leu Ala Gln Ala Ser Val Arg Lys
65                  70                  75                  80

Phe Pro Ile Ala Lys Val Pro Leu Tyr Phe Ala Ala Gln Tyr Leu Gly
                85                  90                  95

Gly Phe Val Gly Ala Ala Leu Val Phe Ala Thr Tyr Lys Asp Ala Ile
            100                 105                 110

Glu His Phe Asp Gln Gly Ile Arg Gln Val Thr Gly Glu Lys Ala Thr
        115                 120                 125

Ala Gly Ile Phe Ala Thr Tyr Pro Arg Pro His Val Ser Thr Leu Thr
    130                 135                 140

Cys Phe Ile Asp Gln Val Ile Ala Thr Gly Ile Met Met Val Cys Val
145                 150                 155                 160

Glu Ala Ile Gly Asp Thr Arg Asn Phe Gly Gly Ile Pro Pro His Ile
                165                 170                 175

His Pro Ile Cys Leu Gly Leu Met Ile Met Ala Ile Ile Phe Ser Phe
            180                 185                 190

Ala Tyr Asn Cys Met Cys Pro Leu
        195                 200
```

<210> SEQ ID NO 2
<211> LENGTH: 317
<212> TYPE: PRT

<213> ORGANISM: Rhipicephalus microplus

<400> SEQUENCE: 2

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe Met Lys Ile Glu Asn
                85                  90                  95

Leu Leu Ile Arg Gln Leu Ile Asn Glu Phe Leu Gly Thr Met Ile Leu
            100                 105                 110

Ile Thr Ile Gly Asp Ser Ile Met Ala Ile Ile Ile Ala Gly Asp Asn
        115                 120                 125

Glu Ser Leu Ala Ala Cys Val Gly Pro Leu Gly Trp Gly Val Ala Ile
130                 135                 140

Tyr Val Ala Val Gln Ile Ser Gly Gly Val Ser Ser His Leu Asn Pro
145                 150                 155                 160

Ala Val Thr Leu Ala Gln Ala Ser Val Arg Lys Phe Pro Ile Ala Lys
                165                 170                 175

Val Pro Leu Tyr Phe Ala Ala Gln Tyr Leu Gly Gly Phe Val Gly Ala
            180                 185                 190

Ala Leu Val Phe Ala Thr Tyr Lys Asp Ala Ile Glu His Phe Asp Gln
        195                 200                 205

Gly Ile Arg Gln Val Thr Gly Glu Lys Ala Thr Ala Gly Ile Phe Ala
    210                 215                 220

Thr Tyr Pro Arg Pro His Val Ser Thr Leu Thr Cys Phe Ile Asp Gln
225                 230                 235                 240

Val Ile Ala Thr Gly Ile Met Met Val Cys Val Glu Ala Ile Gly Asp
                245                 250                 255

Thr Arg Asn Phe Gly Gly Ile Pro Pro His Ile His Pro Ile Cys Leu
            260                 265                 270

Gly Leu Met Ile Met Ala Ile Ile Phe Ser Phe Ala Tyr Asn Cys Met
        275                 280                 285

Cys Pro Ala Ala Ala Ser Phe Leu Glu Gln Lys Leu Ile Ser Glu Glu
    290                 295                 300

Asp Leu Asn Ser Ala Val Asp His His His His His His
305                 310                 315

<210> SEQ ID NO 3
<211> LENGTH: 226
<212> TYPE: PRT
<213> ORGANISM: Rhipicephalus microplus

<400> SEQUENCE: 3

Met Glu Ile Glu Asn Leu Leu Ile Arg Gln Leu Ile Asn Glu Phe Leu
1               5                   10                  15

Gly Thr Met Ile Leu Ile Thr Ile Gly Asp Ser Ile Met Ala Ile Ile
            20                  25                  30

Ile Ala Gly Asp Asn Glu Ser Leu Ala Ala Cys Val Gly Pro Leu Gly

```
                35                  40                  45
Trp Gly Val Ala Ile Tyr Val Ala Val Gln Ile Ser Gly Gly Val Ser
 50                  55                  60

Ser His Leu Asn Pro Ala Val Thr Leu Ala Gln Ala Ser Val Arg Lys
 65                  70                  75                  80

Phe Pro Ile Ala Lys Val Pro Leu Tyr Phe Ala Ala Gln Tyr Leu Gly
                 85                  90                  95

Gly Phe Val Gly Ala Ala Leu Val Phe Ala Thr Tyr Lys Asp Ala Ile
                100                 105                 110

Glu His Phe Asp Gln Gly Ile Arg Gln Val Thr Gly Glu Lys Ala Thr
            115                 120                 125

Ala Gly Ile Phe Ala Thr Tyr Pro Arg Pro His Val Ser Thr Leu Thr
        130                 135                 140

Cys Phe Ile Asp Gln Val Ile Ala Thr Gly Ile Met Met Val Cys Val
145                 150                 155                 160

Glu Ala Ile Gly Asp Thr Arg Asn Phe Gly Gly Ile Pro Pro His Ile
                165                 170                 175

His Pro Ile Cys Leu Gly Leu Met Ile Met Ala Ile Ile Phe Ser Phe
            180                 185                 190

Ala Tyr Asn Cys Met Cys Leu Glu Ser Arg Gly Pro Phe Glu Gln Lys
        195                 200                 205

Leu Ile Ser Glu Glu Asp Leu Asn Met His Thr Gly His His His
    210                 215                 220

His His
225

<210> SEQ ID NO 4
<211> LENGTH: 198
<212> TYPE: PRT
<213> ORGANISM: Rhipicephalus microplus

<400> SEQUENCE: 4

Met Glu Ile Glu Asn Leu Leu Ile Arg Gln Leu Ile Asn Glu Phe Leu
 1               5                  10                  15

Gly Thr Met Ile Leu Ile Thr Ile Gly Asp Ser Ile Met Ala Ile Ile
                20                  25                  30

Ile Ala Gly Asp Asn Glu Ser Leu Ala Ala Cys Val Gly Pro Leu Gly
            35                  40                  45

Trp Gly Val Ala Ile Tyr Val Ala Val Gln Ile Ser Gly Gly Val Ser
 50                  55                  60

Ser His Leu Asn Pro Ala Val Thr Leu Ala Gln Ala Ser Val Arg Lys
 65                  70                  75                  80

Phe Pro Ile Ala Lys Val Pro Leu Tyr Phe Ala Ala Gln Tyr Leu Gly
                 85                  90                  95

Gly Phe Val Gly Ala Ala Leu Val Phe Ala Thr Tyr Lys Asp Ala Ile
                100                 105                 110

Glu His Phe Asp Gln Gly Ile Arg Gln Val Thr Gly Glu Lys Ala Thr
            115                 120                 125

Ala Gly Ile Phe Ala Thr Tyr Pro Arg Pro His Val Ser Thr Leu Thr
        130                 135                 140

Cys Phe Ile Asp Gln Val Ile Ala Thr Gly Ile Met Met Val Cys Val
145                 150                 155                 160

Glu Ala Ile Gly Asp Thr Arg Asn Phe Gly Gly Ile Pro Pro His Ile
                165                 170                 175
```

His Pro Ile Cys Leu Gly Leu Met Ile Met Ala Ile Ile Phe Ser Phe
            180                 185                 190

Ala Tyr Asn Cys Met Cys
        195

<210> SEQ ID NO 5
<211> LENGTH: 947
<212> TYPE: DNA
<213> ORGANISM: Rhipicephalus microplus

<400> SEQUENCE: 5

```
aagcagtggt atcaacgcag agtacgcggg ggggctggga aaagctgcta gcatcaactc    60
ggcttctagc ttggggtctc gcaccgcgcc tcgagcccga ccagcctgcg gtggcgccgt   120
ctcgctgaaa gggggaaaga ggaaagagaa agaagaaaag aaaaatatcg ccggcatcgg   180
cgacgaaggc ggagcagcaa tgcgatcgtc agagcacgca tttcgacggt gagattcgga   240
agctcgaagg cgtcgccggc actgcgagaa agccggtgaa gtactttggg accgccgcgt   300
aggcgtcttg acagtccgct cccgaggcaa cgacgacacg ctccaagatg aagatcgaga   360
acctgctcat acggcagctc atcaacgagt tcctcggaac aatgattcta attactatcg   420
gcgactccat catggccatc atcatcgccg gtgacaacga gtctctggct gcttgcgtgg   480
ggcccttggg atgggcgtc gccatctacg tggccgtgca atctccgga ggagtctcgt    540
cccacctgaa tcctgccgtg acgctggccc aggcgtccgt gcgcaagttt ccgatcgcca   600
aagtgccgct atacttcgcg gctcagtacc tgggtggctt cgtcggtgcg gcgctcgtgt   660
ttgccaccta caaagacgct attgaacact tcgaccaggg aatccgccaa gtgacgggag   720
agaaggccac ggctggtata tttgcaactt accccagacc acacgtctcc actctgacct   780
gcttcattga tcaggtcatc gcaacgggca taatgatggt gtgcgtcgag ccatcggcg    840
acactcgcaa cttcggcggc attccgccgc acattcaccc aatctgcttg ggtctcatga   900
tcatggctat tatcttcagt ttcgcctaca actgcatgtg cccgctc                947
```

<210> SEQ ID NO 6
<211> LENGTH: 954
<212> TYPE: DNA
<213> ORGANISM: Rhipicephalus microplus

<400> SEQUENCE: 6

```
atgagatttc cttcaatttt tactgctgtt ttattcgcag catcctccgc attagctgct    60
ccagtcaaca ctacaacaga agatgaaacg gcacaaattc cggctgaagc tgtcatcggt   120
tactcagatt tagaagggga tttcgatgtt gctgttttgc cattttccaa cagcacaaat   180
aacgggttat tgtttataaa tactactatt gccagcattg ctgctaaaga agaaggggta   240
tctctcgaga aaagagaggc tgaagctgaa ttcatgaaga tcgagaacct gctcatacgg   300
cagctcatca cgagttcct cggaacaatg attctaatta ctatcggcga ctccatcatg   360
gccatcatca tcgccggtga caacgagtct ctggctgctt gcgtggggcc cttgggatgg   420
ggcgtcgcca tctacgtggc cgtgcaaatc tccggaggag tctcgtccca cctgaatcct   480
gccgtgacgc tggcccaggc gtccgtgcgc aagtttccga tcgccaaagt gccgctatac   540
ttcgcggctc agtacctggg tggcttcgtc ggtgcggcgc tcgtgtttgc cacctacaaa   600
gacgctattg aacacttcga ccagggaatc cgccaagtga cgggagagaa ggccacggct   660
ggtatatttg caacttaccc cagaccacac gtctccactc tgacctgctt cattgatcag   720
gtcatcgcaa cgggcataat gatggtgtgc gtcgaggcca tcggcgacac tcgcaacttc   780
```

| | |
|---|---|
| ggcggcattc cgccgcacat tcacccaatc tgcttgggtc tcatgatcat ggctattatc | 840 |
| ttcagtttcg cctacaactg catgtgcccg gcggccgcca gctttctaga acaaaaactc | 900 |
| atctcagaag aggatctgaa tagcgccgtc gaccatcatc atcatcatca ttga | 954 |

<210> SEQ ID NO 7
<211> LENGTH: 684
<212> TYPE: DNA
<213> ORGANISM: Rhipicephalus microplus

<400> SEQUENCE: 7

| | |
|---|---|
| aagatggaga tcgagaacct gctcatacgg cagctcatca acgagttcct cggaacaatg | 60 |
| attctaatta ctatcggcga ctccatcatg ccatcatca tcgccggtga caacgagtct | 120 |
| ctggctgctt gcgtggggcc cttgggatgg ggcgtcgcca tctacgtggc cgtgcaaatc | 180 |
| tccggaggag tctcgtccca cctgaatcct gccgtgacgc tggcccaggc gtccgtgcgc | 240 |
| aagtttccga tcgccaaagt gccgctatac ttcgcggctc agtacctggg tggcttcgtc | 300 |
| ggtgcggcgc tcgtgtttgc cacctacaaa gacgctattg aacacttcga ccagggaatc | 360 |
| cgccaagtga cgggagagaa ggccacggct ggtatatttg caacttaccc cagaccacac | 420 |
| gtctccactc tgacctgctt cattgatcag gtcatcgcaa cgggcataat gatggtgtgc | 480 |
| gtcgaggcca tcgcgacac tcgcaacttc ggcggcattc cgccgcacat tcacccaatc | 540 |
| tgcttgggtc tcatgatcat ggctattatc ttcagtttcg cctacaactg catgtgcctc | 600 |
| gagtctagag ggcccttcga acaaaaactc atctcagaag aggatctgaa tatgcatacc | 660 |
| ggtcatcatc accatcacca ttga | 684 |

<210> SEQ ID NO 8
<211> LENGTH: 595
<212> TYPE: DNA
<213> ORGANISM: Rhipicephalus microplus

<400> SEQUENCE: 8

| | |
|---|---|
| atggagatcg agaacctgct catacggcag ctcatcaacg agttcctcgg aacaatgatt | 60 |
| ctaattacta tcggcgactc catcatggcc atcatcatcg ccggtgacaa cgagtctctg | 120 |
| gctgcttgcg tggggccctt gggatggggc gtcgccatct acgtggccgt gcaaatctcc | 180 |
| ggaggagtct cgtcccacct gaatcctgcc gtgacgctgg cccaggcgtc cgtgcgcaag | 240 |
| tttccgatcg ccaaagtgcc gctatacttc gcggctcagt acctgggtgg cttcgtcggt | 300 |
| gcggcgctcg tgtttgccac ctacaaagac gctattgaac acttcgacca gggaatccgc | 360 |
| caagtgacgg gagagaaggc cacggctggt atatttgcaa cttaccccag accacacgtc | 420 |
| tccactctga cctgcttcat tgatcaggtc atcgcaacgg gcataatgat ggtgtgcgtc | 480 |
| gaggccatcg cgacactcg caacttcggc ggcattccgc cgcacattca cccaatctgc | 540 |
| ttgggtctca tgatcatggc tattatcttc agtttcgcct acaactgcat gtgcc | 595 |

<210> SEQ ID NO 9
<211> LENGTH: 595
<212> TYPE: DNA
<213> ORGANISM: Rhipicephalus microplus

<400> SEQUENCE: 9

| | |
|---|---|
| atgaagattg agaacttgtt gattagacaa ttgattaacg agttcttggg tactatgatt | 60 |
| ttgattacta ttggtgactc tattatggct attattattg ctggtgacaa cgagtctttg | 120 |

-continued

```
gctgcttgcg ttggtccatt gggttggggt gttgctattt acgttgctgt tcaaatttct    180
ggtggtgttt cttctcactt gaatccagct gttactttgg ctcaagcttc tgttagaaag    240
tttccaattg ctaaagttcc attgtacttc gctgctcaat acttgggtgg tttcgttggt    300
gctgctttgg tttttgctac ttacaaagac gctattgaac acttcgacca aggtattaga    360
caagttactg gtgagaaggc tactgctggt atttttgcta cttacccaag accacacgtt    420
tctactttga cttgcttcat tgatcaagtt attgctactg gtattatgat ggtttgcgtt    480
gaggctattg gtgacactag aaacttcggt ggtattccac cacacattca cccaatttgc    540
ttgggtttga tgattatggc tattattttc tctttcgctt acaactgcat gtgcc         595
```